(12) United States Patent
Rattan et al.

(10) Patent No.: US 7,773,769 B2
(45) Date of Patent: Aug. 10, 2010

(54) METHOD OF AND APPARATUS FOR DETECTING DEGRADATION OF VISUAL PERFORMANCE

(75) Inventors: Rishi Rattan, London (GB); John Millington Wild, South Glamorgan (GB)

(73) Assignee: University College Cardiff Consultants Limited (GB)

( * ) Notice: Subject to any disclaimer, the term of this patent is extended or adjusted under 35 U.S.C. 154(b) by 804 days.

(21) Appl. No.: 11/729,287

(22) Filed: Mar. 28, 2007

(65) Prior Publication Data

US 2007/0242854 A1 Oct. 18, 2007

(30) Foreign Application Priority Data

Apr. 3, 2006 (GB) .................................. 0606680.7

(51) Int. Cl.
G06K 9/00 (2006.01)
A61B 3/14 (2006.01)

(52) U.S. Cl. ........................ 382/100; 382/275; 351/208

(58) Field of Classification Search ................. 382/100, 382/103, 106, 107, 115, 128, 129, 130, 131, 382/132, 133, 134, 162, 165, 167, 168, 172, 382/181, 254, 260, 274, 275, 276, 291, 305, 382/312, 216; 600/558; 351/223, 205, 208; 348/441

See application file for complete search history.

(56) References Cited

U.S. PATENT DOCUMENTS

| | | | | |
|---|---|---|---|---|
| 5,694,199 A | * | 12/1997 | Rodriguez | ................... 351/223 |
| 6,045,515 A | * | 4/2000 | Lawton | ...................... 600/558 |
| 7,016,539 B1 | * | 3/2006 | Silver et al. | .................. 382/216 |
| 7,408,587 B2 | * | 8/2008 | Matsutani et al. | ........... 348/441 |
| 7,431,457 B2 | * | 10/2008 | Chernyak | .................... 351/208 |
| 7,513,619 B2 | * | 4/2009 | Lacombe et al. | ............ 351/205 |
| 2003/0081176 A1 | | 5/2003 | Stewart | |
| 2003/0223038 A1 | | 12/2003 | Alster | |

FOREIGN PATENT DOCUMENTS

EP 1 397 991 3/2004

* cited by examiner

*Primary Examiner*—Seyed Azarian
(74) *Attorney, Agent, or Firm*—Reising Ethington P.C.

(57) ABSTRACT

An apparatus for characterising a subject's visual response, comprising a data processor, a display and an input device, wherein the data processor is arranged to present evaluation images at different positions on the display such that they occur at different positions within the subject's field of view, and wherein each evaluation image comprises a contribution of at least two items selected from a list comprising: a base image, a test image, and a noise image, and wherein the data processor is responsive to the input device such that the subject can indicate whether they can see the test image in the evaluation image, and the data processor is further arranged to evaluate the subject's responses so as to give an indication of one or more of visual efficiency, internal noise and visual sensitivity as a function of position within the subjects field of view.

19 Claims, 6 Drawing Sheets

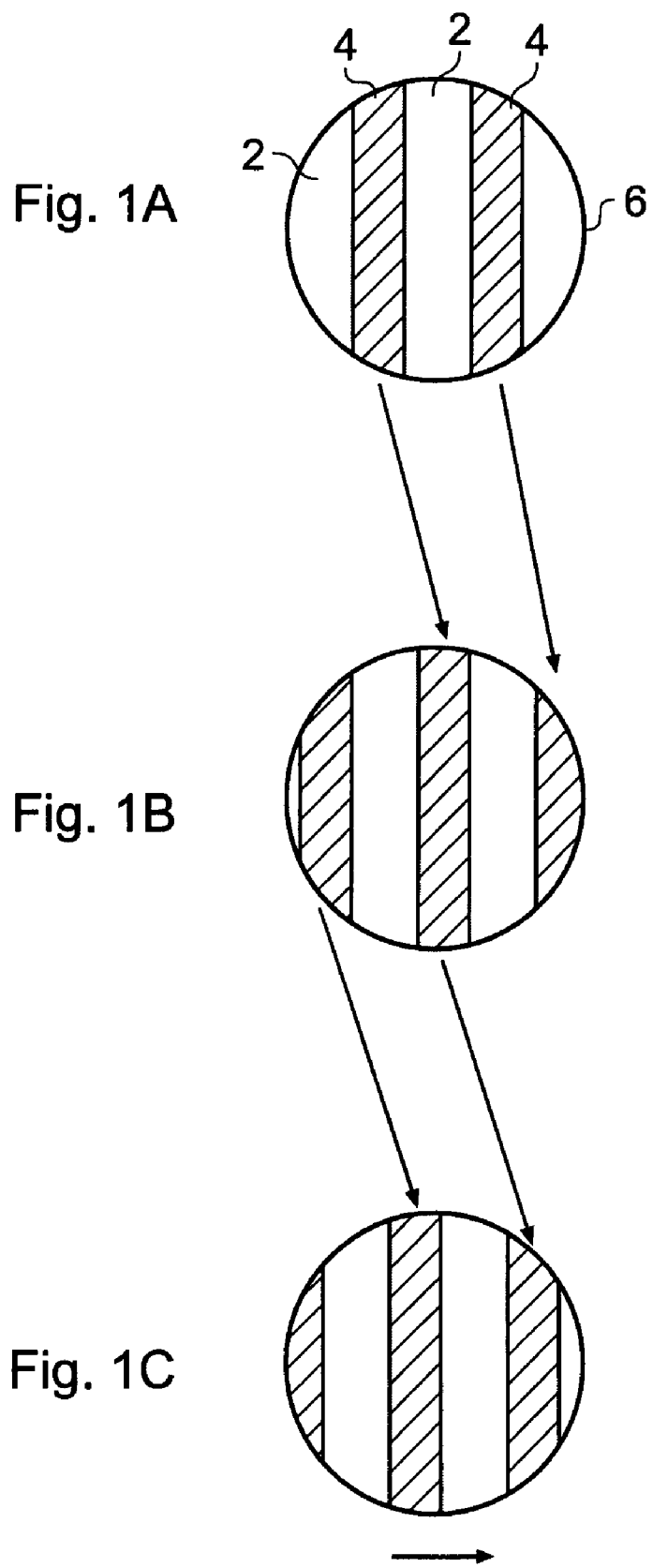

METHOD OF AND APPARATUS FOR DETECTING DEGRADATION OF VISUAL PERFORMANCE

FIELD OF THE INVENTION

The present invention relates to a method of and apparatus for detecting degradation of a person's visual response.

BACKGROUND OF THE INVENTION

Cells within the retina can be characterised in terms which are used by Engineers to measure the performance of detectors. Thus, cells or regions on the retina can be investigated in order to determine their sensitivity, for example to identify a contrasting pattern, and also to determine their internal noise and efficiency.

SUMMARY OF THE INVENTION

According to a first aspect of the present invention there is provided an apparatus for characterising a subject's visual response, comprising a data processor, a display and an input device, wherein the data processor is arranged to present evaluation images at different positions on the display such that they occur at different positions within the subject's field of view, and wherein each evaluation image comprises a contribution of at least two items selected from a list comprising:
 a base image
 a test image, and
 a noise image,
 and wherein the data processor is responsive to the input device such that the subject can indicate whether they can see the test image in the evaluation image, and the data processor is further arranged to evaluate the subject's responses so as to give an indication of one or more of visual efficiency, internal noise and visual sensitivity as a function of position within the subject's field of view.

Advantageously the apparatus is operable to characterise the sensitivity of the eye in two phases. In a first phase a series of first phase images are provided which comprise the base image and varying contributions from the test image. Thus the intensity of the test image can be varied to determine the limit in the intensity difference that the subject is able to resolve as a function of position within the field of view.

In a second phase noise from the noise image is introduced in combination with the test image and the base image.

Thus, in one embodiment of the invention there is provided an apparatus for testing visual response which comprises:
 a test presentation device for presenting a first test image to a user at different positions within a users field of view and recording a user's response, and to add noise to the first test image or a further test image to create a second test image and to present it to the user at different positions with a user's field of view and record a user's response; and
 a data processor adapted to process the responses of the user in response to the first and second test images to provide measurements of one or more of visual sensitivity, internal noise and visual efficiency, each as a function of position within a user's field of view.

The first test image may be a substantially uniform image having an intensity and/or colour that matches the average intensity and/or colour of the second test image. The first test image may include a first test pattern.

Preferably the first test pattern is selected to test a user's ability to resolve contrasts in intensity and/or colour. The first test pattern may comprise alternating regions of colour or intensity. The pattern may be distinct from the background or may be provided by setting a background within the field of view to a user to a chosen intensity and colour and then imposing a change to the intensity and colour in a test region and monitoring the subject's response to that change.

Advantageously the first test pattern has a smooth gradation between lighter sections and darker sections within the pattern, or a smooth gradation between a first colour and a second colour, and back again. Preferably the pattern has a direction of motion imposed upon it. Advantageously the pattern may have two or more directions of motion and the user is required to indicate which direction of motion the pattern has.

Advantageously the test presentation device includes a user input device, such as a keyboard or joystick and a timer for monitoring the time between presentation of the test pattern to the user and the user making an input in order to indicate which direction of motion has been applied to the first test pattern or whether the test pattern exists at that time. The first test presentation device may be arranged to reduce the contrast in the first test pattern each time the user correctly identifies the motion of the pattern within a predetermined time, and to increase the intensity in the first test pattern when the user fails to identify the direction of motion within a predetermined time or incorrectly identifies the direction of motion.

Advantageously the test pattern is presented in a spatially limited form so as to test the user's response at different positions within their field of view and the response for each position is monitored individually such that the level of contrast presented to the user as the test progresses varies with position in a user's field of view in accordance with the user's ability to resolve the pattern.

After performing the first test in order to characterise a user's sensitivity within various regions of their field of view as the function of position within their field of view the second test is initiated in which random or pseudorandom noise is superimposed on a test pattern, preferably the first test pattern, and the tests are repeated. The noise masks the test pattern. The test may be performed with varying intensities of the test pattern and varying intensities of noise. The tests are, as before, limited in their spatial extent in the user's field of view and presented to different regions of the user's field of view so as to characterise their visual response. Advantageously, though not necessarily, the signal to noise ratio may be kept to a predetermined value during the test. A constant signal to noise ratio could be maintained by using noise intensities that reduce the user's sensitivity to the test signal by a factor of three or more.

In an alternative embodiment of the invention users may be shown a sequence of images and asked to identify images that contain a test pattern or test image. In general a user is presented with pairs of images, i.e. the first test image and the second test image (although in a random order). One of the images has the test image or pattern in it—optionally with superimposed noise—whereas the other one of the images does not include the test image or pattern, but may include the noise. The user then has to distinguish between the images to indicate which one included the test image or pattern. This is done merely be indicating whether they think the test pattern is in the first one of the pair of images or the second one of the pair of images.

Once the first and second tests are completed, the data processor analyses the results in order to obtain measurements of sensitivity, internal noise and efficiency as the function of position within a user's field of view.

Hitherto tests seeking to determine visual efficiency have presented test patterns to only a single region, or alternatively the entirety, of a user's field of view. This means that such tests have not had the ability to determine degradation of parts of a user's field of view. These tests have also involved multiple, time consuming measures that may confound or degrade the responses of elderly users and others at risk of suffering from a variety of eye-related disease.

Furthermore, such prior art tests have had to use calibrated display devices in order to get meaningful results. Whilst the present invention benefits from being run on a calibrated display device, it can also usefully be implemented using non-calibrated displays, for example as might be found on a user's home or work personal computer. Although the use in a non-calibrated mode means that the sensitivity, colour performance and ambient lighting conditions cannot be assessed, the test can still be used to determine whether some portions of a user's visual response have degraded with regard to other portions. This in itself can be sufficient to enable a warning to be given to a user to prompt them to seek an examination from a qualified practitioner.

It is also expected that certain diseases will be characterised by performance degradations that follow a particular spatial pattern and that these patterns can be detected as an aid to diagnosis of the underlying cause of the visual degradation.

According to a second aspect of the present invention there is provided a method of characterising a subject's visual response, comprising presenting a plurality of evaluation images at different positions within a subject's field of view, wherein each image comprises a contribution of at least two items selected from a list comprising:

i) a base image;

ii) a test image, and iii) a noise image and receiving an indication from a subject as to whether they can see the test image within the evaluation image, and processing the subject's response to the evaluation images so as to evaluate at least one item selected from a list comprising visual sensitivity, internal noise and visual efficiency, each as a function of position within the subject's field of view.

According to a third aspect of the present invention there is provided a method of testing a subject's visual response, comprising:

performing a first test in which a first test pattern is presented to a user at different positions within their field of view and with different intensities and the user's response is recorded;

performing a second test in which a second test pattern comprising noise superimposed on the first test pattern is presented to a user at different portions within their field of view and with different intensities and the user's response is recorded; and analysing the responses from the first and second tests in order to determine measurements of a user's visual efficiency and internal noise as a function of position within their field of view.

According to a fourth aspect of the present invention there is provided a computer program product for causing a data processor to perform the method according to the second or third aspect.

BRIEF DESCRIPTION OF THE DRAWINGS

The present invention will further be described, by way of example only, with reference to the accompanying Figures, in which:

FIGS. 1a to FIG. 1c schematically illustrates a first test image to be presented to a user;

DESCRIPTION OF PREFERRED EMBODIMENTS OF THE PRESENT INVENTION

Figure 3:
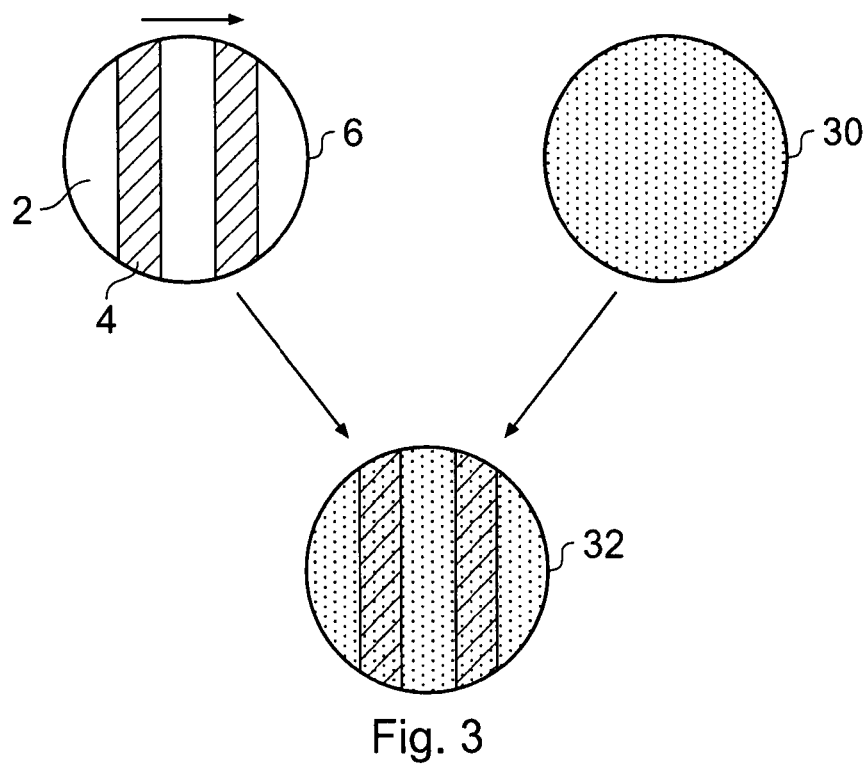
FIG. 3 schematically illustrates modification of the first test pattern to form the second test pattern.

It is reasonable to expect that each cell within the human eye has a limit to its sensitivity. This corresponds with our own experience of finding it difficult to see in the dark. It can also be expected, when considering the human visual system from an engineering viewpoint, that cells generate internal noise. It has been hypothesised that cells which are beginning to suffer from damage, for example due to glaucoma, start to work harder in order to maintain their performance, and if you like to stay alive, and that this additional work that the cell does results in a further degradation of its noise performance. It is therefore expected that the onset of some conditions that result in degradation of visual performance might be detected by measuring efficiency and internal noise within a cell and that the noise figure may allow a disease to be identified before the user experiences any perceptible degradation in their visual performance. This is particularly important with some diseases, such as glaucoma, where the effects of the disease cannot be reversed but current treatment regimes do enable the progression of the disease to be slowed, if not halted.

The present invention seeks to characterise an eye's performance at different portions of a user's field of view. In order to do this, tests of efficiency and internal noise are performed.

FIGS. 1a to 1c schematically illustrate a first test pattern. The test pattern could comprise a static test image, for example as shown in FIG. 1a. However, in one embodiment of the invention the image translates as shown in FIGS. 1a to 1c. The pattern comprises vertically orientated regions 2 and 4 of differing intensity and/or colour. For ease of illustration the regions have been drawn as having sharp transitions in intensity but they could equally have smoothly varying gradations in intensity as, for example, might be expressed by a sinusoidal function. The regions 2 and 4 are constrained to lie within a window 6 so as to constrain the extent of the pattern such that it only subtends a relatively small and well defined region of the user's field of view. Although the window 6 has been illustrated as being circular, it is not limited to being circular and other shapes such as rectangular and square windows may be used.

During the test the window 6 is presented at a first time instant and the position of the window 6 is held constant for a predetermined period of time but the light and dark regions 2 and 4 within the window 6 are caused to translate so as to simulate a motion of the test pattern. In the examples shown in FIGS. 1a to 1c, each region in FIGS. 1b and 1c have moved slightly to the right of the corresponding position for that region in the preceding figures and hence this pattern tends to move to the right. As a region moves to the right hand side of the window 6 a new region is introduced on the left thereby making sure that the pattern becomes replenished. During the test, each time the pattern is presented within a window a random choice is made by the data processor as to whether the pattern will drift to the right or to the left. The pattern may be orientated in any direction and preferably its direction of drift is perpendicular to its direction of orientation.

Figure 2:
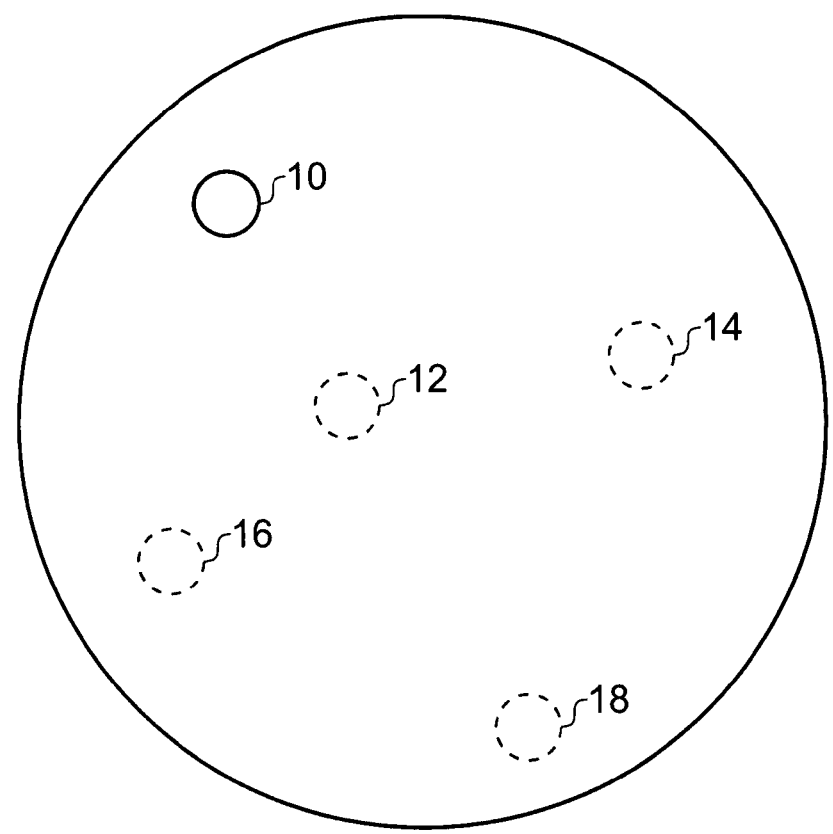
FIG. 2 schematically illustrates the presentation of the first test patterns to various locations within a user's field of view.

Once the pattern has been presented, the user then signals to the data processor that they have identified the existence of the pattern by moving an input device such as a joystick, to the left or right (or other direction) as appropriate to match the direction of motion of the pattern. The time between the presentation of the window and the pattern therein, and the user correctly detecting the motion of the pattern is measured and recorded. In use, the pattern is presented at various positions within a user's field of view, as schematically represented in FIG. 2 where, at a first instance, the window 6 containing the pattern is presented at position 10 and the measurement of the user's response time taken, and subsequent presentations occurs at positions 12, 14, 16, 18 and so on until such time as the user's visual response has been sufficiently mapped in order to characterise it.

The same area will be subjected to multiple presentations of the test pattern. Thus, assuming that an initial test pattern had been presented to area 10 of the user's field of view and that they had correctly identified the direction of motion of the test pattern in a sufficiently short period of time, then later on in the test the test pattern is re-presented to area 10 but with a contrast between the light region 2 and the dark region 4 being reduced such that both areas more closely correspond to a general background which can be regarded as a base image presented on the display in regions outside of the window 6. During the first phase of the test, the intensity difference between the regions 2 and 4 of the test pattern becomes reduced to the limit of the user's ability to distinguish the pattern.

The test then moves on to a second phase in which, as schematically illustrated in FIG. 3, a random noise mask 30 is added to the test window 6 containing the alternating bands 2 and 4 so as to generate a noisy test pattern 32. Alternatively noise may be added to the entirety of the image shown on the display. This noisy test pattern is then presented to the user, repeating the tests as carried out in the first part of the test procedure, such that the user has to distinguish the direction of motion of the alternating bands within the noisy test pattern and the noisy test pattern is presented within a window 6 at various positions within a user's field of view. As before, if a user correctly guesses the direction of motion, then the intensity difference between the light and dark bands is reduced. The test operator can determine whether the noise power of the noise pattern remains constant throughout the test or whether it varies as a function of the intensity difference between the light and dark bands, 2 and 4, respectively, such that the signal to noise ratio in the test pattern remains constant.

Following completion of the first and second test sequences, the results of the tests are then analysed on an area by area basis within the user's field of view such that, for example, for a region 10 the first test result corresponding to that region is retrieved from a computer memory, and a second test result corresponding to that region is also retrieved and then the results are analysed.

Figure 4:
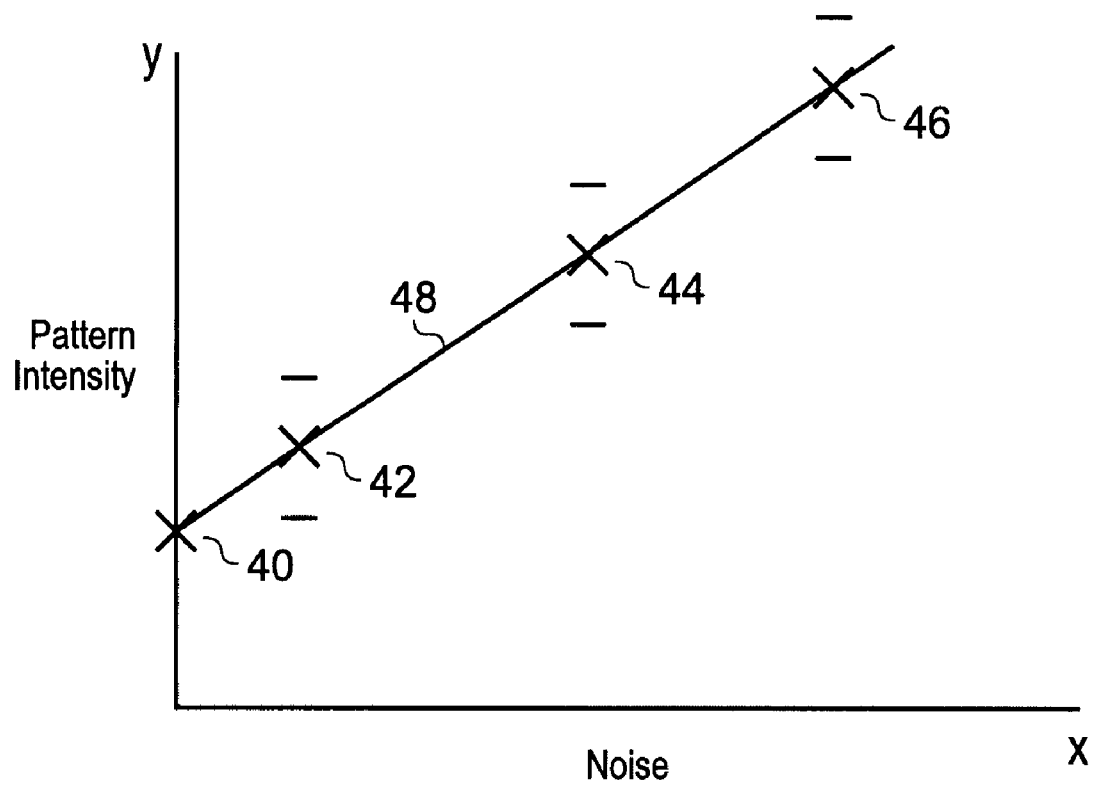
FIG. 4 schematically illustrates how the results of the first and second tests can be used to characterise a user's visual response.

FIG. 4 schematically illustrates, for a given region, the limit of pattern intensity that a user could distinguish plotted with respect to the power of the noise mask superimposed on the test pattern. Thus, when no noise was added (corresponding to the first test) a user can distinguish between the bars at a pattern intensity designated 40. As the noise power is increased, then the pattern intensity (that is the difference in intensity between the light and dark bands) also needs to be increased before the user can distinguish it. Results at first, second and third levels of noise designated 42, 44 and 46 are shown in FIG. 4. Four individual noise measurements are shown in FIG. 4, although in practise it is expected that two will be preferred, so as to shorten the time thereby avoiding the subject becoming bored. Thus, if only, for example, measurements 42 and 46 exist then the line 48 joining the measurement points must be assumed to be a straight line and hence can be characterised only in terms of its gradient and its intercept point within the X axis. Using only these measurements may allow for the test to be presented on any un-calibrated system. The errors of an un-calibrated system would alter the noise mask and the pattern equally, leaving the resultant signal-to-noise ratio unaffected. Assessing two points alone makes the test more applicable to the elderly and others at risk of eye-related disease. The first measurement relates to moderate noise intensity that reduces the user's sensitivity by a factor of substantially three. This type of noise may consist of a variety of luminance levels; seen as various shades of grey (it is termed Gaussian noise). The second measurement involves a much stronger noise mask, which reduces the user's sensitivity by a factor of at least nine. This type of noise consists of two distinct luminance levels; seen as black and white (it is termed Binary noise). The corresponding noise intensities are significantly different, such that the two measurements are far apart on the X axis, thereby ensuring a more accurate slope with only two points of reference. If the slope is extrapolated to the left of the Y axis, its intercept point on the X axis represents a measurement of the intrinsic (internal) noise within the user's visual system whereas the gradient of the graph is an indicator of the efficiency of the user's visual system. In general, the user's efficiency is the inverse of the gradient of the graph shown in FIG. 4.

This analysis is repeated for the test measurements so as to build up a "map" showing both internal noise and visual efficiency as a function of position within the user's field of view.

Figure 5:
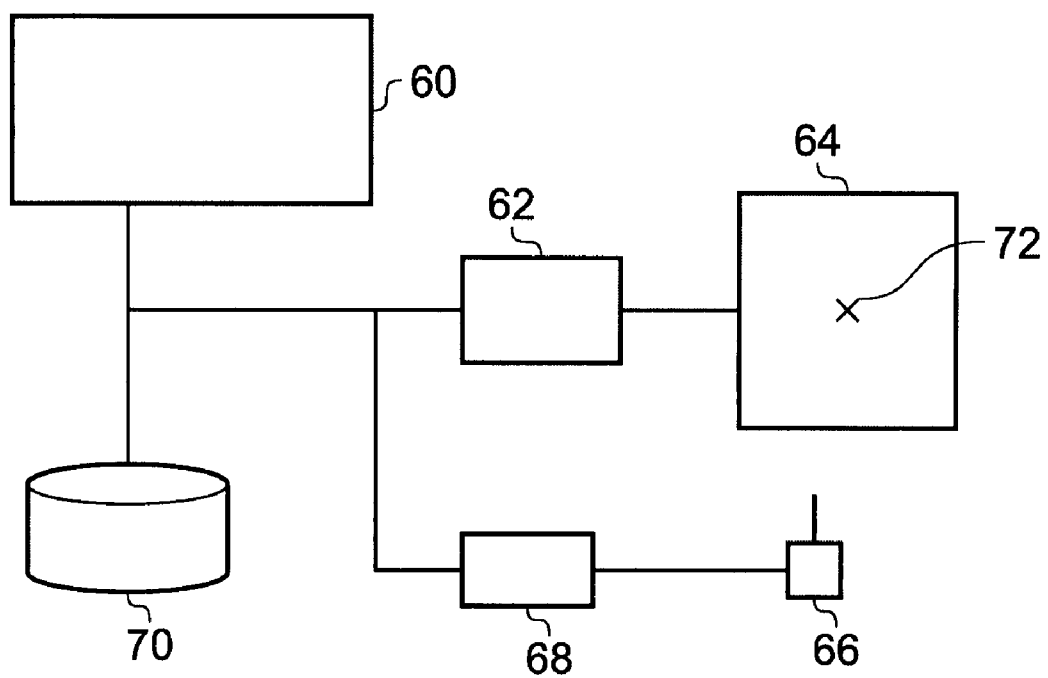
FIG. 5 schematically illustrates an apparatus for performing the invention.

FIG. 5 is a diagram schematically illustrating an apparatus constituting an embodiment of the present invention. The apparatus comprises a data processor 60 in communication with a graphics card 62 which in turn controls a display device 64, for example an LCD display.

The data processor 60 is also in communication with an input device 66, such as a joystick via a suitable interface card 68. A memory comprising one or more of short term volatile storage and long term non-volatile storage is also in communication with the data processor 60 and is designated 70. In use, the data processor 60 retrieves instructions from the memory 70 to cause it to present the first test pattern to various portions of the display screen 64 and to record the user's motions of the joystick 66 as a response. During the test the user should have a single point of fixation and therefore the data processor 60 also causes a target 72 to be displayed. The user should maintain their gaze on the target 72 during the test. Following completion of the first stage of the test, the data processor adds the noise mask and commences the second phase of the test again causing the test patterns to be displayed at various regions of the display 64 and recording the user's response. Once the tests have been completed, the data processor is then adapted to compare the test results in order to derive, and store and/or output numerical or graphical representations of the user's internal noise figures and efficiency measurements as a function of position within their field of view.

The data processor may also be arranged to perform region or contour analysis in order to identify regions having similar levels of performance, i.e. noise level or efficiency in order to identify patterns of performance within the user's response. These patterns may then be compared with a database in order to determine if the patterns correlate with any patterns within the database which are indicative of a condition or disease.

Each of the user's eyes is tested individually.

Hitherto the test has been described as occurring in two distinct phases, which can be regarded as characterisation of a user's ability to see the test image/pattern in the absence of noise in a first phase, and then a second phase in which noise is added to the test pattern and the user again has to indicate whether they can see the test pattern. A validation of the user's response is provided by the fact that they need to identify the direction of motion within the pattern.

These distinct phases, phase 1 and phase 2, were presented at different periods of time.

It can be appreciated that these different parts of the test do not in fact need to be separated in time and that the computer can present the test corresponding to phase 1 and phase 2 in an intermingled sequence to the user.

In a second embodiment of the invention the data processor presents a sequence of evaluation images prior to the user. Each evaluation image is built up of several image components.

The first component is a base image, which is generally a uniform colour that fills the entire display and forms a background. To this base image one or both of a test image and a noise image may be added.

The test image for simplicity may be a grid of alternating light and dark bars, which can transition either abruptly or smoothly with one or another.

The test image is framed in a window and can be combined with the base image so as to alter the base image only in the region enclosed by the window. As before the intensity of the test image is variable so that the perturbation it makes to the base image within the window is also variable. The window can be placed in any one of a plurality of locations on display. The display is positioned with respect to the user, for example using a chin rest or other head restraint, such that the position of a window on the display can be mapped onto a position within a user's field of view.

Figure 6A:
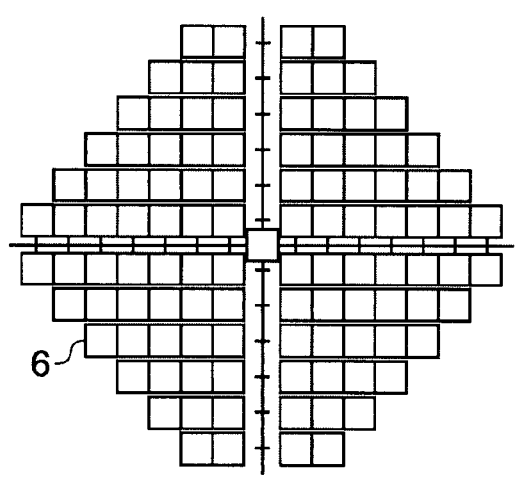
FIG. 6a compares a field of view test grid of the present invention with a prior art "light spot" stimuli grid shown in FIG. 6b.
Figure 6B:
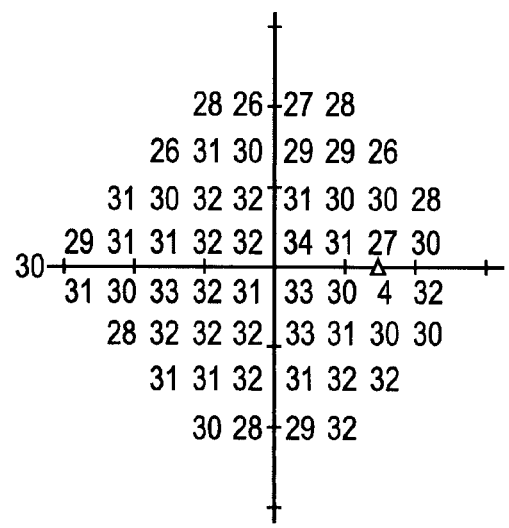

FIG. 6a illustrates a map of the positions where the windows 6 are placed within a users field of view. A camera (not shown) may be used to track the direction of gaze of the user to ensure that they are looking the correct direction during the test, and to discard results obtained when the user is not looking in the correct direction. It can be seen that the window positions have been chosen to coincide with the discrete "light spot" stimuli locations of the prior art and shown in FIG. 6b.

Noise can be also added to the base image or to the combination of the base image and the test image. Image pairs are then presented in succession where none of the evaluation images contains a test image, only one of them (either the first image or the second image) contains the test image, or they both do. The relative intensities of the test image and the noise image can vary within each pair of images, and between pairs of images. In this way it is possible to take multiple readings at a given position within a user's field of view to qualify the limit of pattern intensity versus noise intensity for that position (i.e. as shown in FIG. 4) so as to determine internal noise and visual efficiency.

Figure 7:
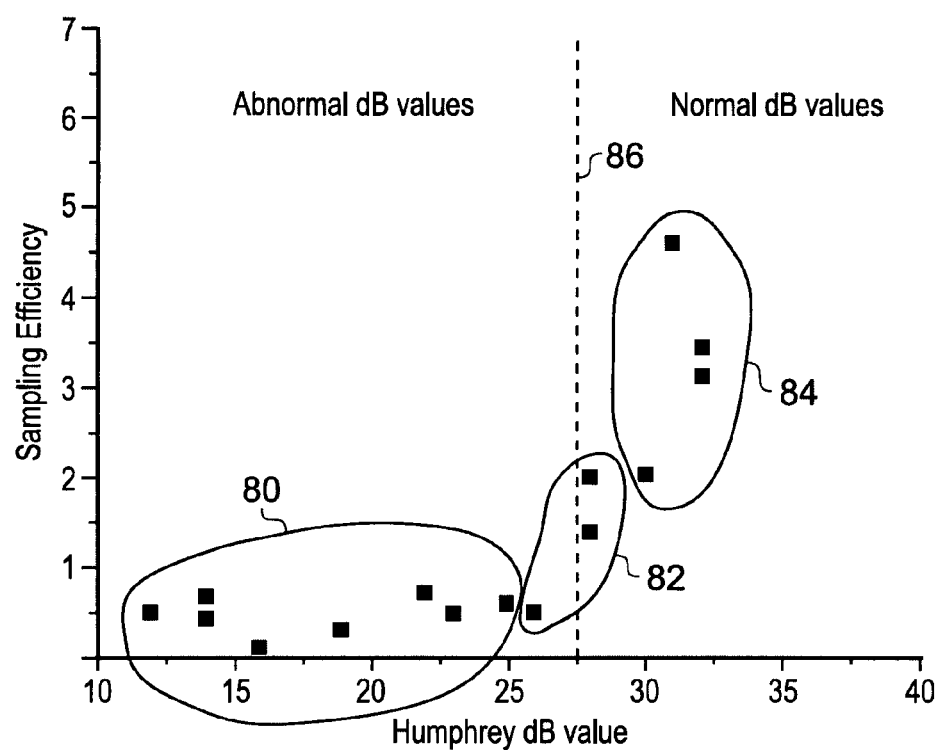
FIG. 7 shows exemplary results from three subjects.

FIG. 7 shows a graph of visual efficiency (the gradient in FIG. 4) for a number of locations within a field of view for three test subjects. The results in the regions 80 and 82 were obtained from individuals suffering from glaucoma. The results in region 84 came from a healthy subject. The chain vertical line 86 separates the normal and abnormal dB values accordingly to conventional probability indices.

Figure 8:
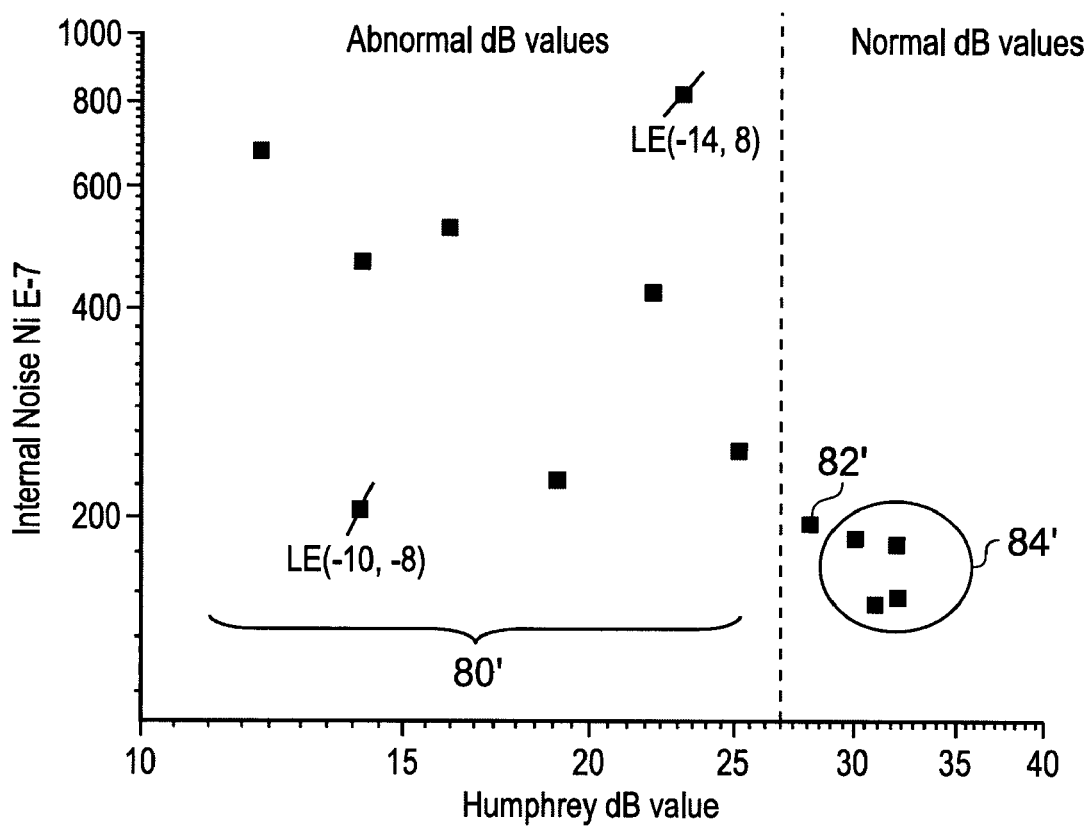
FIG. 8 shows measurements of internal noise from three subjects using the present invention.

FIG. 8 shows noise estimate results for the same individuals. Here region 80' designates the results obtained from the person with glaucoma and designated 80 in FIG. 7. Similarly the single result 82' comes from the same person as the results designated 82 in FIG. 7. Only one result was measured for this individual due to the extent of glaucomatous damage.

It can be seen that the internal noise value falls with improving sensitivity. This is indicative of glaucoma.

Two points in region 80 have been struck out as one point (−10, 8) was found to be surrounded by regions of high sensitivity which may cause an apparent reduction in measured internal noise, whereas the other point (−14, 8) shows elevated internal noise, but was found in conventional tests to be surrounded by areas of poor sensitivity.

It is thus possible to provide a sensitive yet robust test in order to detect degradation of a person's visual system.

The invention claimed is:

1. An apparatus for characterising a subject's visual response, and comprising a data processor, a display, and an input device; wherein:
   the data processor is arranged to present evaluation images at different positions on the display such that they occur at different positions within the subject's field of view;
   each evaluation image comprises a contribution of at least two items selected from a list comprising:
   a base image,
   a test image comprising alternating regions of color or intensity, and
   a noise image;
   a plurality of the evaluation images are formed of a base image, a test image and a noise image so as to assess the limit of the subject's ability to identify the test image in the presence of noise as a function of position; and
   the data processor is responsive to the input device such that the subject can indicate whether the subject can see the test image in the evaluation image, and the data processor is further arranged to evaluate the subject's responses so as to give an indication of internal noise and one or more indications of visual efficiency and visual sensitivity as a function of position within the subject's field of view.

2. An apparatus as claimed in claim 1, in which the data processor is arranged to present the base image and varying contributions of the test image to a subject so as to assess the limit of the subject's ability to identify the test image as a function of position.

3. An apparatus as claimed in claim 1, in which the data processor varies the noise power of the noise image so as to characterise, as a function of position within a subject's field of view, the subject's ability to identify a test image in the presence of noise.

4. An apparatus as claimed in claim 1, in which, for a given position in a subject's field of view, the data processor is arranged to analyse the subject's response of minimum test image intensity versus noise to determine visual sensitivity at that position.

5. An apparatus as claimed in claim 1, in which for a given position in a subject's field of view the data processor is arranged to analyse the subject's response of minimum discernable test image intensity versus noise to estimate a noise value at that position.

6. An apparatus as claimed in claim 1, in which the data processor is arranged to output the values of visual sensitivity, efficiency or internal noise as a graph or a map.

7. An apparatus as claimed in claim 1, wherein the data processor is arranged to examine visual performance as a function of position within a subject's field of view to look for trends indicative of disease, and to output its results.

8. An apparatus as claimed in claim 1, wherein the apparatus is arranged to present a first test image to a subject at different positions within a subject's field of view and to record a subject's response; to add noise to the first test image or a further test image to create a second test image and to present it to a subject's field of view and record the subject's response; and then to process the subject's response to the first and second test images.

9. An apparatus as claimed in claim 1, in which the test image comprises alternating bands of differing intensity.

10. A method of using a processor to characterise a subject's visual response, the method comprising
 presenting a plurality of evaluation images at different positions within a subject's field of view, wherein each image comprises a contribution of at least two items selected from a list comprising:
 i) a base image,
 ii) a test image combined with the base image and presented at varying intensities and varying positions within a subject's field of view; and
 iii) a noise image
 and receiving an indication from a subject as to whether the subject can see the test image within the evaluation image and identify the test image as a function of position;
 and processing the subject's response to the evaluation images so as to evaluate at least one item selected from a list comprising visual sensitivity, internal noise and visual efficiency, each as a function of position within the subject's field of view.

11. A method as claimed in claim 10, in which the base image defines a background.

12. A method as claimed in claim 11, in which noise is added to the base image.

13. A method as claimed in claim 10, in which noise is further added to the test image to assess the limit of the subject's ability to identify the test image in the presence of noise as a function of position.

14. A method as claimed in claim 13, in which the noise power is varied.

15. A method as claimed in claim 10, in which an analysis of a subject's minimum perceptible test image intensity versus noise intensity is performed, as a function of position in the subject's field of view, to determine visual sensitivity as a function of position.

16. A method as claimed in claim 10, in which an analysis, as a function of position, is performed, of the minimum perceptible test image intensity versus noise in order to assess noise as a function of position.

17. A method of using a processor to test a subject's visual response comprising:
 performing a first test in which a first test pattern is presented to a subject against a base image that defines a background and at different positions within the subject's field of view and with different intensities, and recording the subject's response and determining from the subject's response the subject's ability to identify the test pattern as a function of position;
 performing a second test in which a second test pattern comprising noise added to the first test pattern or an equivalent thereof is presented to a subject at different positions within the subject's field of view and with different intensities of noise or different intensities of the first test pattern and recording the subject's response, and analysing the responses to determine measurements of the subject's visual efficiency and internal noise as a function of position within the subject's field of view.

18. A method as claimed in claim 17, in which the subject's response is an indication by the subject that the subject can see the first test pattern.

19. A method as claimed in claim 17, in which the first test pattern comprises alternating regions of different intensity.

* * * * *